(12) United States Patent  
Thornton

(10) Patent No.: US 6,743,183 B1  
(45) Date of Patent: Jun. 1, 2004

(54) SIMULTANEOUS STIMULATION OF AN AUDITORY SYSTEM

(75) Inventor: Aaron Thornton, West Des Moines, IA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 252 days.

(21) Appl. No.: 10/124,154

(22) Filed: Apr. 17, 2002

(51) Int. Cl.⁷ .................................................. A61B 5/00
(52) U.S. Cl. ........................................ 600/559; 600/544
(58) Field of Search ................................ 600/544, 559

(56) References Cited

U.S. PATENT DOCUMENTS

| | | | | |
|---|---|---|---|---|
| 5,413,114 A | * | 5/1995 | Zurek et al. | 600/559 |
| 5,697,379 A | * | 12/1997 | Neely et al. | 600/544 |
| 6,200,273 B1 | * | 3/2001 | Sininger et al. | 600/559 |
| 6,231,521 B1 | * | 5/2001 | Zoth et al. | 600/559 |

OTHER PUBLICATIONS

Marsh, R. "Concurrent Right and Left Ear Auditory Brain Stem Response Recording", *Ear & Hearing*, vol. 14, No. 3 (1993).

\* cited by examiner

*Primary Examiner*—Max F. Hindenburg
*Assistant Examiner*—David J McCrosky
(74) *Attorney, Agent, or Firm*—Fish & Richardson P.C.

(57) ABSTRACT

A method for measuring an electrophysiologic response of a sensory system includes stimulating the sensory system with a first stimulus train having stimuli temporally separated from each other by a first inter-stimulus interval and simultaneously stimulating the sensory system with a second stimulus train having stimuli temporally separated from each other by a second inter-stimulus interval different from the first inter-stimulus interval. A response signal is then sampled at a first frequency corresponding to the first inter-stimulus interval, thereby obtaining a first response train. The first response train is then processed to suppress a contaminant caused by the second stimulus train.

30 Claims, 4 Drawing Sheets

SIMULTANEOUS STIMULATION OF AN AUDITORY SYSTEM

FIELD OF INVENTION

This invention relates to the measurement of an electrophysiologic response, and in particular, to the measurement of electrophysiologic responses to auditory stimuli.

BACKGROUND

In making a diagnosis, it is often useful to have the patient's cooperation. This is particularly true in the diagnosis of disease involving sensory pathways to the brain. For example, a straightforward way to assess a patient's hearing is to simply ask the patient whether he can hear particular tones having various frequencies and amplitudes.

In many cases, one takes for granted that a patient will be able to answer such questions. However, in some cases, a patient cannot communicate his perception. This occurs most frequently when the patient is an infant, or when the patient is unconscious. In a veterinary setting, it is rare to encounter a patient that can accurately communicate perception at all.

One approach to evaluating an infant's hearing is to make a sound and to then measure an evoked response associated with that sound. This evoked response is typically an electrophysiologic signal generated in response to the sound and traveling between the inner ear and the brain along various neural pathways, one of which includes the auditory brainstem. This signal is thus referred to as the "auditory brainstem-response," hereafter referred to as the "ABR."

The ABR is typically only a small component of any measured electrophysiologic signal. In most cases, a noise component arising from other, predominantly myogenic, activity within the patient dwarfs the ABR. The amplitude of the ABR typically ranges from approximately 1 microvolt, for easily audible sounds, to as low as 20 nanovolts, for sounds at the threshold of normal hearing. The noise amplitude present in a measured electrophysiologic signal, however, is typically much larger. Typical noise levels range from between 2 microvolts to as much as 2 millivolts. The resulting signal-to-noise ratio thus ranges between −6 dB and −40 dB.

One approach to increasing the signal-to-noise ratio is to exploit differences between the additive properties of the ABR and that of the background noise. This typically includes applying a repetitive auditory stimulus (a series of clicks, for example) and sampling the electrophysiologic signal following each such stimulus. The resulting samples are then averaged. The ABR component of the samples add linearly, whereas the background electrophysiologic noise, being essentially random, does not. As a result, the effect of noise tends to diminish with the number of samples.

Since the signal-to-noise ratio depends on the number of samples, one could, in principle, more rapidly measure the ABR by reducing the interval between auditory stimuli. Unfortunately, the impulse response of the human auditory system is not, itself, an impulse. Instead, the response to an impulsive stimulus, such as a click or a tone, is a curve representing a pattern of activity that occupies a finite interval of time. As a result, when the interval between a present stimulus and its preceding stimulus is too short, the response to the preceding stimulus may not have died down before the onset of the response to the present stimulus. This means that a sample intended to capture a response to the present stimulus can be contaminated by the tail end of the response curve for the preceding stimulus. This effect limits how close together two stimuli can be, and hence how quickly a particular signal-to-noise ratio can be achieved.

SUMMARY

The invention avoids the foregoing limitation by stimulating the auditory system in a manner that enables an apparatus to remove, from the response due to a particular stimulus, the residual effects of responses due to preceding stimuli. The invention is based on the recognition that by simultaneously stimulating the auditory system with at least two pulse trains having slightly different pulse repetition frequencies, one can average out the responses due to preceding stimuli.

In one aspect, the invention provides for measurement of an electrophysiologic response of a sensory system. The method includes simultaneously stimulating the sensory system with two stimulus trains. The first stimulus train has stimuli temporally separated from each other by a first inter-stimulus interval, whereas the second stimulus train has stimuli separated from each other by a second inter-stimulus interval different from the first inter-stimulus interval. A response signal is then sampled at a first frequency corresponding to the first inter-stimulus interval, thereby obtaining a first response train. The first response train is then processed to suppress a contaminant caused by the second stimulus train.

In one practice of the invention, a second response train is generated by sampling the response signal at a second frequency corresponding to the second inter-stimulus interval. This second response train is then processed to suppress a contaminant attributable to the first stimulus train.

One way to sample a response signal is to define a sequence of sampling windows separated from each other by multiples of the first inter-stimulus interval. During each of a plurality of the sampling windows, samples representative of the electrophysiologic response are obtained. These samples are temporally separated from each other by multiples of an inter-sample interval.

In some practices of the invention, the first and second inter-stimulus intervals can be separated by an integer number of inter-sample intervals. In other practices of the invention, the first and second inter-stimulus intervals can be selected such that all samples from a sampling window are equally likely to be contaminated by a contaminant caused by the second stimulus train. In yet other practices of the invention, the first and second inter-stimulus intervals are selected such that an extent to which a response due to the stimulus train overlaps a sampling window changes between sampling windows.

The invention also includes a data-acquisition system for measuring the response of a sensory system. Such a system includes first and second stimulators simultaneously stimulating the sensory system with first and second stimulus trains. The first stimulus train has stimuli temporally separated from each other by a first inter-stimulus interval. The second stimulus train has stimuli temporally separated from each other by a second inter-stimulus interval different from the first inter-stimulus interval. The system further includes a first sampler for sampling a response signal at a first frequency corresponding to the first inter-stimulus interval, thereby obtaining a first response train, and a processor configured for processing the first response train to suppress a contaminant caused by the second stimulus train.

Additional embodiments include a second sampler for sampling the response signal at a second frequency corresponding to the second inter-stimulus interval, thereby generating a second response train. In these embodiments, the processor is configured to process the second response train by suppressing a contaminant caused by the first stimulus train.

In some embodiments, the first sampler is configured to define a sequence of sampling windows separated from each other by multiples of the first inter-stimulus interval, and to obtain samples representative of the electrophysiologic response during each of a plurality of the sampling windows. The samples are separated from each other by multiples of an inter-sample interval.

In other embodiments, the second sampler is configured to sample the response at a second inter-stimulus interval that differs from the first inter-stimulus interval by an integer number of inter-sample intervals.

In additional embodiments, the second stimulator is configured to generate stimuli separated by a second inter-stimulus interval, the second inter-stimulus interval being selected such that all samples from a sampling window are equally likely to be contaminated by a contaminant caused by the second stimulus train.

Other embodiments include second samplers configured to generate stimuli separated by a second inter-stimulus interval selected such that an extent to which a response due to the second stimulus train overlaps a sampling window changes between sampling windows.

Additional embodiments include a second stimulator configured to generate stimuli separated by a second inter-stimulus interval selected such that the extent of his overlap varies by an integer multiple of the sampling interval.

These and other features of the invention will be apparent from the following figures, in which:

DETAILED DESCRIPTION

Figure 1:
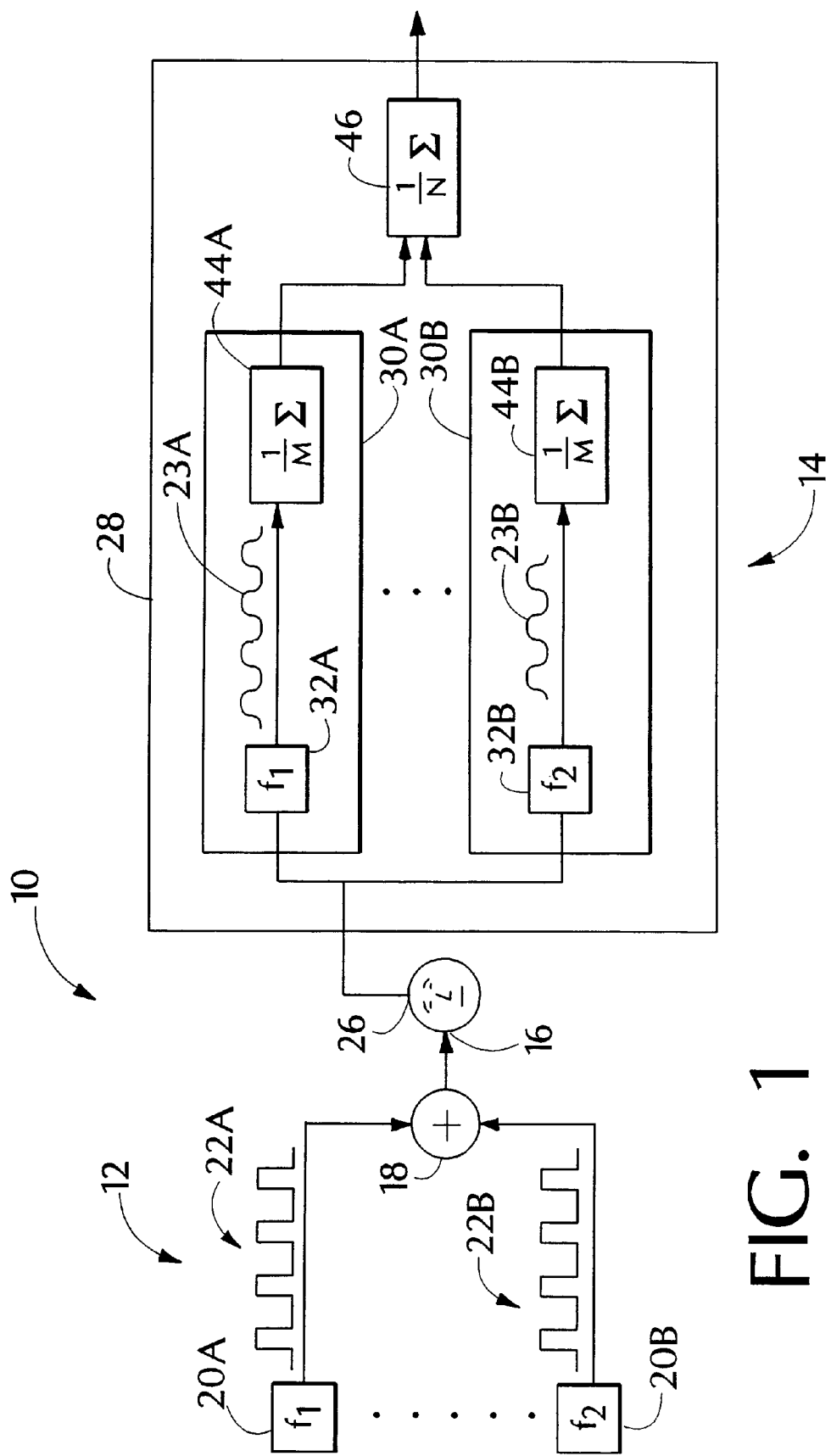
FIG. 1 depicts a system for measurement of electrophysiologic response.

FIG. 1 shows a data-acquisition system 10 that includes a stimulator subsystem 12 and a detector subsystem 14. The stimulator subsystem 12 generates acoustic stimuli and provides those stimuli to an ear of a patient. In a healthy patient, this results in stimulation of the auditory system and a consequent response. The detector subsystem 14 detects responses to stimuli generated by the stimulator subsystem 12 and processes those responses to enhance their signal-to-noise ratio. The data-acquisition system 10 thus enables one to evaluate a patient's hearing without that patient's conscious cooperation.

The stimulator subsystem 12 includes a receiver 16 in acoustic communication with an ear of a patient. The receiver 16 is an acoustic transducer in acoustic communication with the ear of a patient. Examples of receivers 16 include, but are not limited to, loudspeakers and earphones. A summer 18 connected to the receiver 16 combines the outputs of first and second stimulators 20A, 20B and passes the resulting combination to the receiver 16. The first stimulator 20A is configured to generate a sequence of identical acoustic stimuli (hereafter referred to as the "first stimulus train 22A") at a first pulse-repetition frequency.

The second stimulator 20B is configured to generate a sequence of identical acoustic stimuli (hereafter referred to as "the second stimulus train 22B") at a second pulse-repetition frequency that differs from the first pulse-repetition frequency. The periods corresponding to the first and second pulse-repetition frequencies are referred to respectively as the "first and second inter-stimulus intervals." The extent of the difference between the first and second pulse-repetition frequencies will become apparent in a discussion of the detector subsystem 14 below.

The stimuli can be any waveform. However, it is preferable that the waveform be one that approximates an impulse. Suitable waveforms include those generated by clicks or short tones. The stimuli generated by the first stimulator 20A are identical to each other. However, there is no requirement that they be identical to the stimuli generated by the second stimulator 20B.

The pulse-repetition frequency is selected to be as high as possible but not so high as to cause responses from one stimulus to merge with responses to preceding stimuli. The optimal frequency depends on the impulse response of the patient's auditory system. For most patients, the pulse-repetition frequency is no greater than 60 Hz.

Each stimulus evokes an electrophysiologic response in the patient. As a result, both the first and second stimulus trains 22A, 22B result in corresponding first and second response trains 23A, 23B. Each response train 23A, 23B is a sequence of response waveforms, each of which includes a response to a stimulus on one of the stimulus trains. Each response waveform also includes a first extraneous component due to random electrophysiologic noise, a second extraneous component due to responses from preceding stimuli on that response train 23A, and a third extraneous component due to responses from preceding stimuli on other response trains 23B. It is toward the suppression of this third extraneous component that the invention is directed.

Because the first and second pulse-repetition frequencies differ from each other, the stimulus trains generated by the first and second stimulators 20A, 20B will drift relative to each other. As a result, the response trains 23A, 23B due to the first and second stimulus trains 22A, 22B will likewise drift relative to each other. It is this drift that enables the detector subsystem 14 to suppress the third extraneous component.

The detector subsystem 14 includes a probe 26 affixed to the patient's scalp. The probe 26 is in communication with a digital processor 28 executing as many detectors as there are stimulus trains. Thus, in FIG. 1, the probe 26 is in communication with a first and second detector 30A, 30B. As shown herein, a single digital processor 28 executes multiple detectors. However, in an alternative embodiment, a separate first and second digital processors execute the first and second detectors 30A, 30B respectively.

Figure 2:
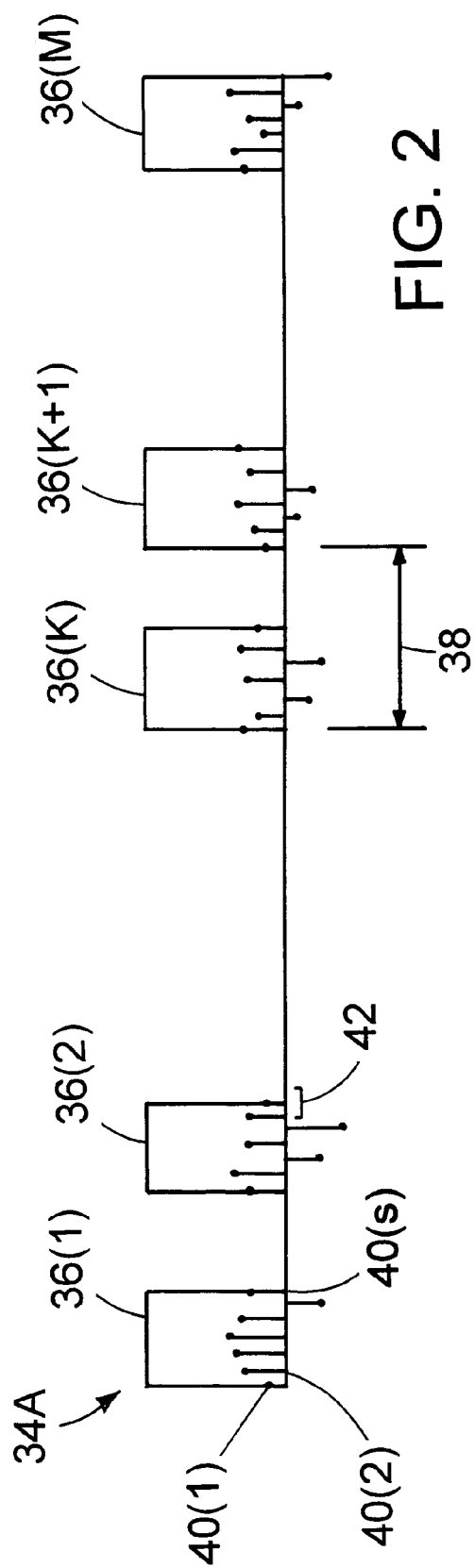
FIGS. 2 and 3 show sampling windows with samples of an electrophysiologic response.

A first sampling process 32A, associated with the first detector 30A, defines a train 34A of sampling windows 36(A)–36(M), as shown in FIG. 2. An interval between sampling windows 36(K), 36(K+1) is selected to correspond to the first pulse-repetition frequency. In particular, the interval between the beginning of a first sampling window 36(K) and the beginning of a second sampling window 36(K+1) immediately following the first sampling window is the first inter-stimulus interval 38.

During a typical sampling window 36(1), the first sampling process 32A obtains several samples 40(1)–40(s) of the waveform. These samples are separated from each other by an inter-sample interval 42. In one practice of the invention, the first sampling process 32A obtains 100 equally-spaced samples during a 10 millisecond sampling window. Hence the inter-sample interval 42 is 0.1 milliseconds.

Figure 3:
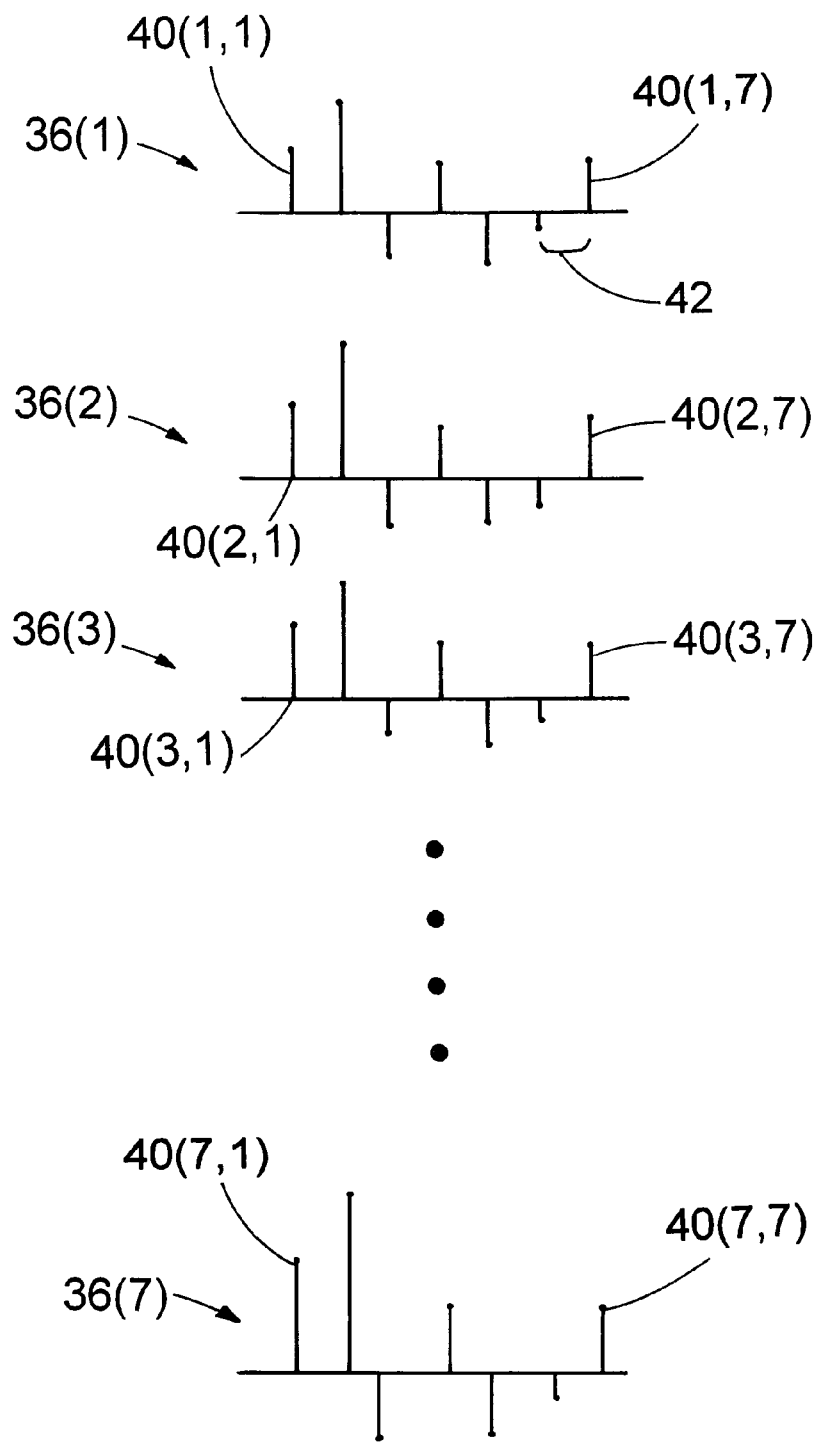

FIG. 3 shows several successive sampling windows 36(1)–36(7) obtained by the first sampling process 32A. A typical sampling window 36(1) includes a number of samples 40(1,1)–40(1,7) separated by the inter-sample interval 42. The sampling windows 36(1)–36(7) are aligned vertically so that corresponding samples 40(1,1), 40(2,1), ... 40(7,1) from successive sampling windows 36(1), 36(2), ... 36(7) lie along the same vertical line, which corresponds to the same lapse of time following a stimulus.

The samples obtained by the first sampling process 32A are provided to a first averaging process 44A. The first averaging process 44A maintains a sum of the values of corresponding samples 40(1,1), 40(2,1) . . . 40(M,1) from each sampling window 36(1)–36(M) and divides the result by the number of sampling windows. The first averaging process 44A thus provides an average corresponding to each of the samples in a sampling window.

The difference between the first and second pulse-repetition frequencies is selected such that the difference between the first and second inter-stimulus intervals is an integer multiple of the inter-sample interval 42. For example, if the first pulse-repetition frequency is 50 Hz, and the inter-sample interval 42 is 0.1 milliseconds, a suitable choice for a second pulse-repetition frequency is 1/.201 Hz (approximately 49.75 Hz). This choice results in first and second inter-stimulus intervals of 20 milliseconds and 20.1 milliseconds respectively. The resulting 0.1 millisecond difference causes the second response train 23B to drift across the sampling windows 36(1)–36(M) defined by the first sampling process 32A, and to do so by one inter-sample interval 42 for each repetition of the second stimulus. As a result, each sample in a sampling window will, in the long run, be contaminated equally by the responses on the second response train 23B.

The second detector 30B includes a second sampling process 34B and a second averaging process 44B that cooperate in a manner identical to that described above in connection with the first detector 30A. However, in the case of the second detector 30B, the second sampling process 34B defines sampling windows on the basis of the second pulse-repetition frequency rather than on the basis of the first pulse-repetition frequency. In particular, the second sampling process 34B defines sampling windows such that the interval between the beginning of a first sampling window and the beginning of a second sampling window immediately following the first sampling window is the second inter-stimulus interval.

During each sampling window, the second sampling process 34B obtains several samples of the waveform. These samples are separated from each other by an inter-sample interval that is identical to, or an integer multiple of, the inter-sample interval 42 used by the first sampling process 32A.

The samples obtained by the second sampling process 34B are provided to the second averaging process 44B, which maintains an average of each sample. The averaging process carried out by the second averaging process 44B is similar to that carried out by the first averaging process 44A. The output of the second averaging process 44B is thus a single average sampling window that contains averaged-values, each one of which is obtained by averaging samples separated by the inter-stimulus interval 38.

In one implementation, when the first and second stimulus trains 22A–B have stimuli of the same frequency and intensity, the output of the first averaging process 44A, together with the output of the second averaging process 44B is provided to a global averaging process 46. The global averaging process 46 sums the averages of corresponding samples as provided by the first and second averaging process 44A, 44B. The output of the global averaging process 46 is a set of values, each of which corresponds to an average of one of the samples in a sampling window.

Figure 4:
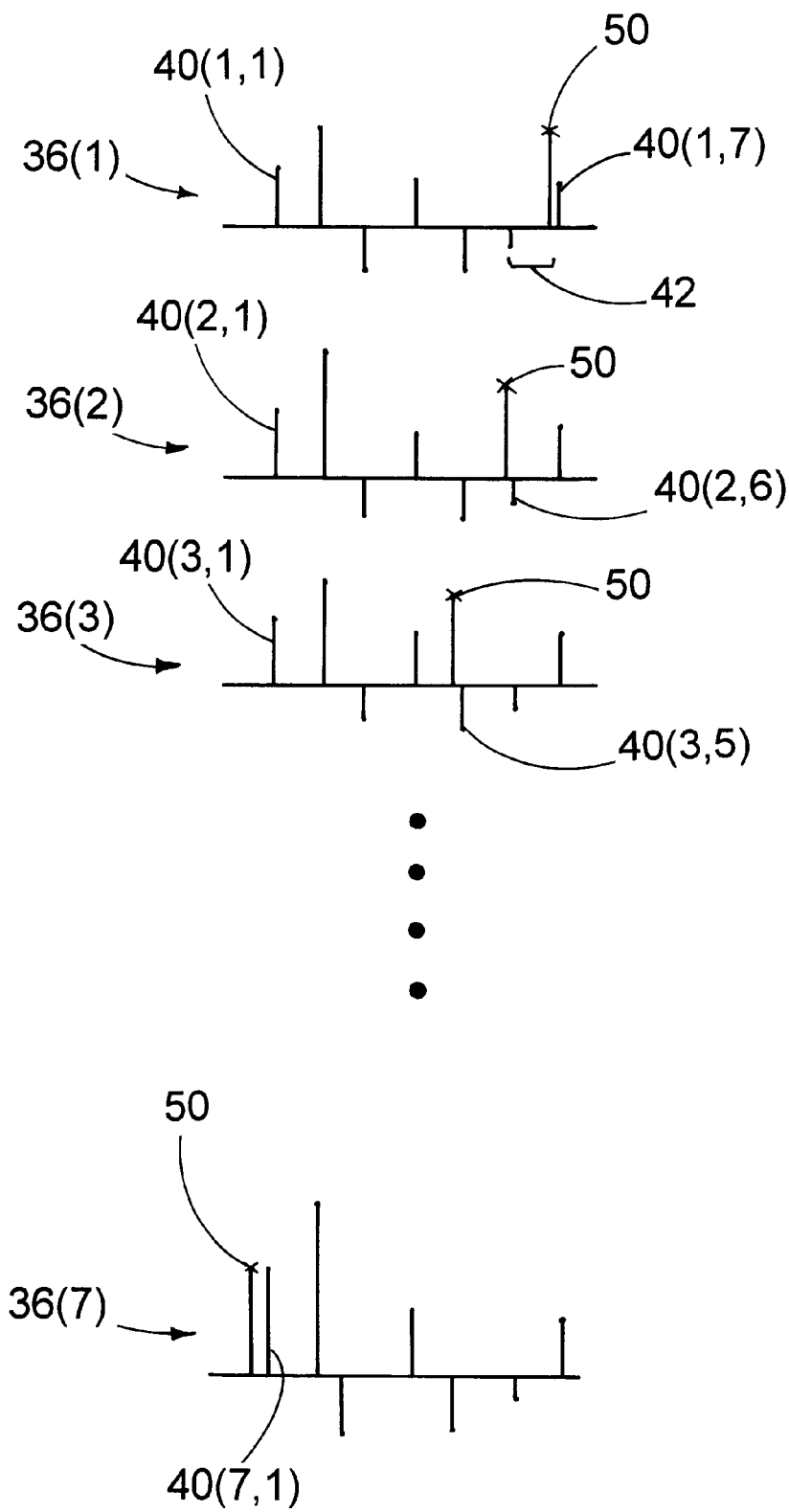
FIG. 4 shows a contaminating response present in the sampling windows of FIG. 3.

FIG. 4 illustrates the manner in which the data-acquisition system 10 reduces the effect of contamination between responses due to different stimulus trains. Like FIG. 3, FIG. 4 shows several successive sampling windows obtained by the first sampling process 32A. Each sampling window includes a number of samples separated by an inter-sample interval 42. The sampling windows are again aligned vertically so that corresponding samples from successive sampling windows lie along the same vertical line.

Also shown in FIG. 4 is a contaminating response 50 caused by stimuli on the second stimulus train 22B. For clarity, the contaminating response 50 is shown as being offset from the samples. However, in fact the contaminating response 50 and the samples are synchronized.

In general, the contaminating response 50 is not a single impulse as shown in FIG. 4 but a waveform having a temporal extent. However, to the extent that the system is linear and time-invariant, any such waveform can be decomposed into a set of shifted and scaled impulses such as that shown in FIG. 4. Hence, the following discussion generalizes to the case of any waveform.

In the first sampling window 36(1), the contaminating response 50 coincides with the last sample 40(1,7) in the sampling window 36(1). Because the second pulse-repetition frequency is slightly lower than the first pulse-repetition frequency, the next stimulus from the second stimulus train 22B is delayed relative to the next stimulus from the first stimulus train 22A. The extent of this delay is one inter-sample interval 42. As a result, the contaminating response 50 is also delayed by one inter-sample interval 42, as shown in the second sampling window of FIG. 4.

For similar reasons, the contaminating response 50 drifts backwards, as shown by successive sampling windows 36(2)–36(7) in FIG. 4. As it drifts backward through the sampling windows, the contaminating response 50 coincides once with each sample. Although the magnitude of the contaminating response 50 may vary randomly as it drifts across the sampling window, after many sampling windows, its value will tend to converge to an average value. Consequently, when the first averaging process 44A obtains its average of each sample, the net effect of the contaminating response 50 is to shift each sample value by a constant value, namely the average value of the contaminating response 50.

The drift of the contaminating response 50 across successive sampling windows thus enables the data-acquisition system 10 to treat the contaminating response 50 as a DC offset that does not affect the shape of the underlying response curve. The DC offset can then be filtered, thereby providing a response in which the third extraneous component is largely suppressed. In practice, the response trains 23A–B are also filtered to cause their long-term average to be zero. As a result, the DC offset noted above will be zero.

A data-acquisition system 10 incorporating the invention is thus able to decontaminate responses due to adjacent stimuli that are too close together. As a result, the constraint on the minimum distance between stimuli is relaxed. This enables one to stimulate more frequently in the same testing period, thereby enabling one to obtain a higher signal-to-noise ratio in a testing period, or alternatively, to test additional aspects of auditory system performance during that same time interval. Alternatively, the testing period for each patient can be shortened, thereby enabling more patients to be tested during that same interval.

As described herein, the data-acquisition system 10 requires two stimulus trains 22A, 22B that have slightly different pulse-repetition frequencies. However, the invention does not preclude having more than two stimulus trains. One could stimulate the auditory system with any number of stimulus trains, provided that any two of those stimulus trains drift relative to each other in the manner described above. In such a case, the detector subsystem 14 would include additional sampling processes configured to define sampling windows at each of the pulse-repetition frequencies.

Also as described herein, the pulse-repetition frequencies are selected such that the contaminating response 50 drifts across the sampling window by one inter-sample interval 42 for each repetition of the first stimulus. However, what is required is that in the long run, each sample in the sampling window is contaminated more or less equally by the contaminating response 50. The particular order in which the individual samples is contaminated is not important. For example, one could vary the pulse-repetition frequencies by pseudo-random sequences having a uniform distribution across the sampling window so that in the long run, the contaminating response 50 will have contaminated each sample equally.

In addition, the first and second stimuli need not be the same stimulus. They can instead be stimuli having different attributes. For example, in one embodiment, the first and second stimuli are tones of different pitches. Such an embodiment enables the auditory system response to be measured at two different pitches simultaneously and in a short testing interval. Alternative embodiments include those in which the first and second stimuli have different intensities or different bandwidths.

The foregoing description illustrates a data-acquisition system 10 for measuring a response of the auditory system. The techniques described herein can, however, be applied to other systems whose impulse response extends over a finite interval. By simultaneously stimulating such systems with two or more stimulus trains having different pulse-repetition frequencies, one can effectively obtain more samples per unit time even though responses from temporally proximate stimuli may overlap with each other.

Having described the invention, and a preferred embodiment thereof, what I claim as new, and secured by letters patent is:

1. A method for measuring an electrophysiologic response of a sensory system, said method comprising:
   stimulating said sensory system with a first stimulus train having stimuli temporally separated from each other by a first inter-stimulus interval;
   simultaneously stimulating said sensory system with a second stimulus train having stimuli temporally separated from each other by a second inter-stimulus interval different from said first inter-stimulus interval;
   sampling a response signal at a first frequency corresponding to said first inter-stimulus interval, thereby obtaining a first response train; and
   processing said first response train to suppress a contaminant caused by said second stimulus train.

2. The method of claim 1, further comprising:
   sampling said response signal at a second frequency corresponding to said second inter-stimulus interval, thereby obtaining a second response train;
   processing said second response train to suppress a contaminant caused by said first stimulus train.

3. The method of claim 1, wherein processing said first response train comprises averaging a set of samples from said first response train to suppress said contaminant attributable to said second stimulus train.

4. The method of claim 1, wherein sampling a response signal comprises:
   defining a sequence of sampling windows separated from each other by multiples of said first inter-stimulus interval; and
   during each of a plurality of said sampling windows, obtaining samples representative of said electrophysiologic response, said samples being separated from each other by multiples of an inter-sample interval.

5. The method of claim 4, further comprising selecting said first and second inter-stimulus intervals to differ by an integer number of inter-sample intervals.

6. The method of claim 5, wherein processing said first response train comprises averaging said samples across a plurality of said sample windows.

7. The method of claim 4, further comprising selecting said first and second inter-stimulus intervals such that all samples from a sampling window are equally likely to be contaminated by a contaminant caused by said second stimulus train.

8. The method of claim 4, further comprising selecting said first and second inter-stimulus intervals such that an extent to which a response due to said stimulus train overlaps a sampling window changes between sampling windows.

9. The method of claim 8, further comprising selecting said first and second inter-stimulus intervals such that said extent varies by an integer multiple of said sampling interval.

10. The method of claim 1, further comprising selecting said sensory system to be an auditory system.

11. The method of claim 10, further comprising selecting said first stimulus train to include stimuli having a first attribute and selecting said second stimulus train to include stimuli having a second attribute different from said first attribute.

12. The method of claim 11, further comprising selecting said first and second attributes from the group consisting of pitch, bandwidth, and intensity.

13. A data acquisition-system for measuring an electrophysiologic response of a sensory system, said system comprising:
   a first stimulator for stimulating said sensory system with a first stimulus train having stimuli temporally separated from each other by a first inter-stimulus interval;
   a second stimulator for simultaneously stimulating said sensory system with a second stimulus train having stimuli temporally separated from each other by a second inter-stimulus interval different from said first inter-stimulus interval;
   a first sampler for sampling a response signal at a first frequency corresponding to said first inter-stimulus interval, thereby obtaining a first response train; and
   a processor configured for processing said first response train to suppress a contaminant caused by said second stimulus train.

14. The system of claim 13, further comprising:
a second sampler for sampling said response signal at a second frequency corresponding to said second inter-stimulus interval, thereby generating a second response train; and
wherein said processor is configured to process said second response train by suppressing a contaminant caused by said first stimulus train.

15. The system of claim 13, wherein said processor is configured to suppress said contaminant attributable to said second stimulus train by averaging a set of samples from said first response train.

16. The system of claim 13, wherein said first sampler is configured to
define a sequence of sampling windows separated from each other by multiples of said first inter-stimulus interval; and to
obtain samples representative of said electrophysiologic response during each of a plurality of said sampling windows, said samples being separated from each other by multiples of an inter-sample interval.

17. The system of claim 16, wherein said second sampler is configured to sample said response at a second inter-stimulus interval that differs from said first inter-stimulus interval by an integer number of inter-sample intervals.

18. The system of claim 17, wherein said processor is configured to execute an averaging process for averaging said samples across a plurality of said sample windows.

19. The system of claim 16, wherein said second stimulator is configured to generate stimuli separated by a second inter-stimulus interval, said second inter-stimulus interval being selected such that all samples from a sampling window are equally likely to be contaminated by a contaminant caused by said second stimulus train.

20. The system of claim 16, wherein said second stimulator is configured to generate stimuli separated by a second inter-stimulus interval, said second inter-stimulus interval being selected such that an extent to which a response due to said second stimulus train overlaps a sampling window changes between sampling windows.

21. The system of claim 20, wherein said second stimulator is configured to generate stimuli separated by a second inter-stimulus interval, said second inter-stimulus interval being selected such that said extent varies by an integer multiple of said sampling interval.

22. A computer-readable medium having encoded thereon software for measuring an electrophysiologic response of a sensory system, said software comprising instructions for:
stimulating said sensory system with a first stimulus train having stimuli temporally separated from each other by a first inter-stimulus interval;
simultaneously stimulating said sensory system with a second stimulus train having stimuli temporally separated from each other by a second inter-stimulus interval different from said first inter-stimulus interval;
sampling a response signal at a first frequency corresponding to said first inter-stimulus interval, thereby obtaining a first response train; and
processing said first response train to suppress a contaminant caused by said second stimulus train.

23. The computer-readable medium of claim 22, wherein said software further comprises instructions for:
sampling said response signal at a second frequency corresponding to said second inter-stimulus interval, thereby obtaining a second response train;
processing said second response train to suppress a contaminant caused by said first stimulus train.

24. The computer-readable medium of claim 22, wherein said instructions for processing said first response train comprise instructions for averaging a set of samples from said first response train to suppress said contaminant attributable to said second stimulus train.

25. The computer-readable medium of claim 22, wherein said instructions for sampling a response signal comprise instructions for:
defining a sequence of sampling windows separated from each other by multiples of said first inter-stimulus interval; and
during each of a plurality of said sampling windows, obtaining samples representative of said electrophysiologic response, said samples being separated from each other by multiples of an inter-sample interval.

26. The computer-readable medium of claim 25, wherein said software further comprises instructions for selecting said first and second inter-stimulus intervals to differ by an integer number of inter-sample intervals.

27. The computer-readable medium of claim 26, wherein said instructions for processing said first response train comprise instructions for averaging said samples across a plurality of said sample windows.

28. The computer-readable medium of claim 25, wherein said software further comprises instructions for selecting said first and second inter-stimulus intervals such that all samples from a sampling window are equally likely to be contaminated by a contaminant caused by said second stimulus train.

29. The computer-readable medium of claim 25, wherein said software further comprises instructions for selecting said first and second inter-stimulus intervals such that an extent to which a response due to said stimulus train overlaps a sampling window changes between sampling windows.

30. The computer-readable medium of claim 29, wherein said software further comprises instructions for selecting said first and second inter-stimulus intervals such that said extent varies by an integer multiple of said sampling interval.

* * * * *